(12) United States Patent
Breitenbach et al.

(10) Patent No.: US 6,221,368 B1
(45) Date of Patent: Apr. 24, 2001

(54) PROCESS FOR PRODUCING SOLID DOSAGE FORMS BY EXTRUSION

(75) Inventors: Jörg Breitenbach, Mannheim; Andreas Kleinke, Ludwigshafen; Stephan Kothrade, Limburgerhof; Joerg Rosenberg, Ellerstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,558

(22) PCT Filed: Sep. 11, 1997

(86) PCT No.: PCT/EP97/04984

§ 371 Date: Mar. 10, 1999

§ 102(e) Date: Mar. 10, 1999

(87) PCT Pub. No.: WO98/10752

PCT Pub. Date: Mar. 19, 1998

(30) Foreign Application Priority Data

Sep. 13, 1996 (DE) ................................ 196 37 479
Aug. 6, 1997 (DE) ................................ 197 34 011

(51) Int. Cl.⁷ .................................................. A61K 9/00
(52) U.S. Cl. ......................... 424/400; 424/497; 424/464
(58) Field of Search .................... 424/400, 497, 424/464

(56) References Cited

U.S. PATENT DOCUMENTS

| | | | |
|---|---|---|---|
| 4,520,172 | 5/1985 | Lehmann et al. | 525/369 |
| 4,801,460 | 1/1989 | Goertz et al. | 424/465 |
| 4,880,585 | 11/1989 | Klimesch et al. | 264/141 |
| 4,957,681 | 9/1990 | Klimesch et al. | 264/211 |
| 5,073,379 | 12/1991 | Klimesch et al. | 424/467 |
| 5,260,074 | 11/1993 | Sipos | 424/497 |
| 5,384,323 | 1/1995 | Bolz et al. | 514/339 |
| 5,552,159 | 9/1996 | Mueller et al. | 424/464 |

FOREIGN PATENT DOCUMENTS

| | | |
|---|---|---|
| 080862 | 6/1983 | (EP) . |
| 590963 | 4/1994 | (EP) . |
| 729748 | 9/1996 | (EP) . |
| 1388786 | 3/1975 | (GB) . |
| 2249957 | 5/1992 | (GB) . |
| 63-222112 | 9/1988 | (JP) . |
| 92/-5774 | 4/1992 | (WO) . |

OTHER PUBLICATIONS

Schmitt, *Res. Discl.*, No. 387, 1996, p. 404.
Fikentscher, *Cell–Chemie*, 13, 1932, 58–64, 71–74.
Houben–Weyl XIV, 1961, 411–420, 192–208.
Sucker et al., *Pharm. Tech.*, 1978 (Table of Contents).
Ford et al., *Pharm. Acta. Helv.*, 61, 1986, 69–88.
Thoma, *Pharm. Ind.*, 51, 1989, 98–101.

*Primary Examiner*—Leon B. Lankford, Jr.
(74) *Attorney, Agent, or Firm*—Dergosits & Noah LLP

(57) ABSTRACT

A process for producing solid dose forms by mixing at least one polymeric binder, with or without at least one active ingredient and with or without conventional additives, and shaping the mixture, where at least one of the components is employed in liquid form.

16 Claims, No Drawings

PROCESS FOR PRODUCING SOLID DOSAGE FORMS BY EXTRUSION

The present invention relates to a process for producing solid pharmaceutical forms by mixing at least one pharmacologically acceptable polymeric binder and at least one pharmaceutical active ingredient, with or without conventional pharmaceutical additives, and extruding. the mixture to give the desired pharmaceutical form.

Conventional processes for producing solid pharmaceutical forms especially tablets, are carried out batchwise and comprise a number of stages. In general, the ingredients of the drug form are first conveyed into a suitable container and then mixed with the addition of a solvent to give a kneadable paste. The paste is then granulated, and the granules are dried and shaped to the desired drug form, for example by compressing them into tablets. Processes of this type are described in relevant text books and, for example, in DE-A-41 41 268 and EP-A-590 963. A grave disadvantage of these processes is the large number of stages and items of apparatus required.

A considerably simpler continuous process for producing solid pharmaceutical forms has been known for some time and entails converting a melt of polymeric binder which contains active ingredients and is free from solvents into the required drug form by injection molding or extrusion and subsequent shaping; see, for example, EP-A-240 904, EP-A-240 906 and EP-A-337 256. Such a process comprises energy-intensive melting of the thermoplastic binder, which is usually in powder form. Furthermore, the technical complexity involved in mixing the binder with other components, such as a pharmaceutical active ingredient or conventional pharmaceutical auxiliaries which are generally in solid form, is relatively great. For example, special solids mixers are required if the mixing is to take place in a separate step before the melting. In this case, there is also the risk that the components of the premix which is fed into the extruder separate, and thus that drugs of nonuniform composition will be produced. On the other hand, the coupling of the melting and mixing steps in the extruder requires a relatively long residence time in a zone with high shear in order to bring about sufficient mixing of the components. This may result in local overheating and damage to the product, especially when a shear- and temperature-sensitive active ingredient is being used. A further disadvantage of using powder-form substances is the formation of dust.

Although it is true that the transport of dry polymers in powder form is less expensive, a large number of pharmacologically appropriate polymers which are used as binders for producing solid pharmaceutical forms are produced as a dispersion or solution. For use in the process described above, the polymers are in a further step always isolated as solids and dried. Direct use of a polymer dispersion or solution as binder, like the use of the auxiliaries in liquid form, has not hitherto been considered.

Polymer dispersions have previously been employed in the production of solid pharmaceutical forms only for applying a coating. For instance, EP 088 951 describes a process for coating solid drug forms using a coating composition which is dispersed in water. To do this, an emulsion polymer is spray-dried and redispersed, and the resulting dispersion is applied, as the coating composition, to the ready-prepared drug form.

The present invention relates to a process for producing solid dose forms by mixing at least one polymeric binder, with or without at least one active ingredient and with or without conventional additives, extruding the mixture and shaping, which comprises employing at least some of the components in liquid form.

For the purposes of the invention, dose forms are all forms suitable for use as drugs, plant treatment agents, feedstuffs and foodstuffs. These include, for example, tablets of whatever shape, pellets, granules, but also larger forms, such as cubes, blocks or cylindrical forms, which can be used in particular as feed or foodstuffs.

For the purposes of the invention polymeric binders are not only natural or synthetic polymers but also meltable substances of low molecular mass, such as sugar alcohols, sugars, fats or waxes.

For the purposes of the invention liquid form means that one of the components employed has been taken up, at least in part, in a solvent or is in the form of a melt. If the component has been taken up in a solvent, this can be in the form of a solution, dispersion, emulsion or suspension.

The dose forms obtainable in accordance with the invention generally comprise:
a) from 0 to 100% by weight, in particular from 0.1 to 50% by weight (based on the overall weight of the dose form) of an active ingredient,
b) from 0 to 100% by weight, in particular from 50 to 99.9% by weight, of a polymeric binder, and
c) with or without additives.

If the dose form is employed for food or feed purposes, the active ingredient may be absent; ie. the dose form can embrace up to 100% of the polymeric binder.

Particularly suitable binders are pharmacologically acceptable polymers. These are physiologically tolerated polymers which are able to dissolve or swell in a physiological environment and to release the active ingredient (if present). It is also important that the processing temperature can be chosen so that, on the one hand, the mixture can be shaped but, on the other hand, there is no damage to the components, especially to the active ingredient. This means that the glass transition temperature of the polymeric binder is preferably below the decomposition temperature of all the components present in the mixture.

The polymeric binder is preferably employed in the form of an aqueous or alcoholic dispersion or solution. Polymer dispersions or solutions which are suitable in accordance with the invention can be obtained by emulsion, suspension or solution polymerization. These processes are known to the skilled worker. Any ancillary substances which might be required for carrying out these processes are likewise a constituent of the binder e according to the invention and are described in detail hereinafter.

Polymer dispersions or solutions which are suitable in accordance with the invention can also be obtained by dispersing or dissolving, respectively, a solid polymer in a dispersant or solvent. For example, polymer can be dissolved in an organic solvent and then an aqueous solution with emulsifiers suitable for dispersing the polymer in water can be stirred into the organic solution first obtained. The primary product of this—provided the organic phase is in excess—is a W/O emulsion. If further emulsifier solution is added, there is ultimately a phase inversion to form a finely disperse O/W emulsion. A dispersion, preferably an aqueous dispersion, can be obtained from this emulsion by evaporating the organic solvents. Ancillary substances which may be employed to implement this process are a constituent of the dispersions or solutions which are appropriate in accordance with the invention and are described in detail hereinafter. However, it is preferably the solutions or dispersions obtained in the preparation of the polymer, with or without prior concentration, which are employed.

Both W/O emulsions and O/W emulsions can be employed in the process according to the invention.

The polymers suitable in accordance with the invention are obtainable by polymerizing ethylenically unsaturated monomers. These include both essentially water-insoluble and essentially water-soluble monomers. They can be employed alone or in a mixture. The relative proportion of water-insoluble or water-soluble monomers, respectively, has a considerable influence on the properties of the resulting polymer. The location and timing of the release of active ingredient can therefore be adjusted to match the pharmaceutical requirements by the choice of polymer.

Suitable essentially water-insoluble monomers are, in particular, monoethylenically unsaturated monomers, such as esters of $\alpha,\beta$-monoethylenically unsaturated mono- and dicarboxylic acids having 3 to 6 C atoms, such as acrylic acid, methacrylic acid, maleic acid, fumaric acid and itaconic acid, with alkanols having in general 1 to 30, preferably 1 to 18 and, in particular, 1 to 12 C atoms, vinyl $C_1$–$C_{18}$-alkyl ethers, vinyl esters of aliphatic $C_1$–$C_{18}$-monocarboxylic acids, and $C_2$–$C_6$ monoolefins. Examples are methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, t-butyl acrylate, t-butyl methacrylate, pentyl acrylate, pentyl methacrylate, n-hexyl acrylate, n-hexyl methacrylate, n-heptyl acrylate, n-heptyl methacrylate, n-octyl acrylate, n-octyl methacrylate, 2-ethylhexyl acrylate, 2-ethylhexyl methacrylate, decyl acrylate, decyl methacrylate, lauryl acrylate, lauryl methacrylate, palmityl acrylate, palmityl methacrylate, stearyl acrylate, stearyl methacrylate, hydrenol acrylate, hydrenol methacrylate, behenyl acrylate or behenyl methacrylate, dimethyl maleate, di-n-butyl maleate, styrene, $\alpha$-methylstyrene, o-chlorostyrene, vinyltoluenes, vinyl ethyl ether, vinyl acetate, vinyl propionate, vinyl-n-butyrate, vinyl laurate, vinyl stearate, ethylene, propylene and butadiene. p Water-soluble monomers are, in particular, $\alpha,\beta$-monoethylenically unsaturated carboxylic acids having 3 to 6 C atoms, such as acrylic acid, methacrylic acid, crotonic acid and maleic acid; acrylamide, methacrylamide; hydroxyalkyl (meth)acrylates, such as hydroxyethyl (meth) acrylate: dialkylaminoalkyl (meth)acrylates, such as dimethylaminoethyl (meth)acrylate; dialkylaminoalkyl(meth) acrylamides, such as dimethylaminoalkyl(meth) acrylamides; and N-vinyllactams, such as N-vinylpyrrolidone or N-vinylcaprolactam.

Particularly suitable polymers which can be obtained from the abovementioned monomers are poly (meth) acrylates, their copolymers with (meth)acrylic acid, polyvinyllactams, polyvinyl esters and copolymers of N-vinyllactams and vinyl esters.

Particularly preferred are, on the one hand, poly(meth) acrylates and their copolymers with (meth)acrylic acid, in particular a copolymer of methacrylic acid and ethyl acrylate, and, on the other hand, polyvinylpyrrolidone and copolymers thereof with vinyl esters, especially a copolymer of N-vinylpyrrolidone and vinyl acetate.

The K values (in accordance with H. Fikentscher, Cellulose-Chamie 13 (1932), pages 58 to 64 and 71 and 74) of the polymers are in a range from 10 to 100, preferably from 12 to 70 and, in particular, from 12 to 35, and for PVP>17, in particular from 20 to 35.

The above-described polymers are preferably prepared by free-radical aqueous emulsion polymerization, so that they are obtained as an aqueous dispersion. Particular preference is given to latex dispersions, by which in macromolecular chemistry there are meant dispersions which comprise semisolid, plastic or elastic particles in very finely dispersed form. Latex particles of this kind have a virtually spherical shape with a diameter of from 0.01 to 1 $\mu$m.

The polymers suitable in accordance with the invention may also include further ancillary substances which play a part in the preparation of these polymers. Such ancillary substances include, for example, the free-radical polymerization initiators, for example peroxides, hydroperoxides, peroxodisulfates, percarbonates, peroxy esters and azo compounds. They decompose under the conditions of extrusion or are decomposed following polymerization by means of an appropriate aftertreatment with reducing agents.

Polymer dispersions and solutions in an aqueous medium are preferred in accordance with the invention. For the purposes of the invention aqueous medium can also be mixtures of water and water-miscible organic liquids. Examples of water-miscible organic liquids are polyols, especially glycols such as ethylene glycol, propylene glycol, 1,3-butylene glycol, diethylene glycol, triethylene glycol, tetraethylene glycol and glycerol, block copolymers of ethylene oxide and propylene oxide, alkoxylated $C_1$–$C_{20}$ alcohols, acetates of glycols and polyglycols, alcohols such as methanol, ethanol, isopropanol and butanol, acetone, tetrahydrofuran, dimethylformamide, N-methylpyrrolidone, or mixtures of these solvents. Where polymerization is conducted in mixtures of water and water-miscible solvents, the proportion of water-miscible solvents in the mixture is up to 75% by weight.

The dispersions suitable in accordance with the invention are preferably prepared using physiologically tolerated emulsifiers or protective colloids as dispersants. This applies both to the implementation of the free-radical polymerization, especially emulsion polymerization, and to the redispersing of solvent-free polymers.

Examples of suitable protective colloids are polyvinyl alcohols, cellulose derivatives, polyvinylpyrrolidone, or copolymers containing vinylpyrrolidone. A detailed description of further suitable protective colloids is given in Houben-Weyl, Methoden der organischen Chemie, Volume XIV/1, Makromolekulare Stoffe [Macromolecular substances], Georg-Thieme-Verlag, Stuttgart, 1961, pp. 411 to 420. It is of course also possible to use mixtures of emulsifiers and/or protective colloids. The dispersants preferably employed are exclusively emulsifiers, whose relative molecular weights, unlike those of the protective colloids, are usually below 1000. They can be anionic, cationic or nonionic in nature. Examples of customary emulsifiers are ethoxylated mono-, di- and trialkylphenols (EO units: 3 to 50, alkyl: $C_4$ to $C_9$), ethoxylated fatty alcohols (EO units: 3 to 50, alkyl: $C_8$ to $C_{36}$), and also alkali metal salts and ammonium salts of alkyl sulfates (alkyl: $C_8$ to $C_{12}$), of sulfuric monoesters with ethoxylated alkanols (EO units: 4 to 30, alkyl: $C_{12}$ to $C_{18}$) and with ethoxylated alkylphenols (EO units: 3 to 50, alkyl: $C_4$ to $C_9$), of alkylsulfonic acids (alkyl: $C_{12}$ to $C_{18}$) and of alkylarylsulfonic acids (alkyl: $C_9$ to $C_{18}$). Other suitable emulsifiers are given in Houben-Weyl, loc. cit., pages 192 to Further useful binders are cellulose derivatives, such as cellulose esters, for example cellulose acetate or cellulose butyrate, cellulose ethers, especially methylcellulose and ethylcellulose, hydroxyalkylcelluloses, especially hydroxymethylcellulose, hydroxypropylcellulose and hydroxyethylcellulose, hydroxyalkylalkylcelluloses, especially hydroxypropylmethylcellulose and hydroxypropylethylcellulose, sodium carboxymethylcellulose, ditylcellulose, cellulose phthalates, especially cellulose acetate phthalate, hydroxypropylmethylcellulose acetate phthalate and hydroxypropylmethylcellulose phthalate, mannans, especially galactomannans, polyvinyl acetate phthalate, shellac, gelatin, pectin, guar flour, starch and degraded starches, starch derivatives, polyvinyl alcohol, dextrin, pullulan, acacia, tragacanth, sodium alginate, propylene glycol alginate, agar or phospholipids.

Other suitable binders are sugar alcohols, such as mannitol, inositol, pentaerythritol, sugars, such as lactose and glucose; and fats and waxes as defined below as flow agents.

It is also possible to add conventional, preferably physiologically acceptable, plasticizing ancillary substances to the binders in order to reduce their glass transition temperature. The amount of plasticizer does not exceed 30% by weight, based on the overall weight of binder and plasticizer, so that storage-stable drug forms are formed which show no cold flow. However, the mixture preferably contains no plasticizer.

Examples of such plasticizers are:

long-chain alcohols, ethylene glycol, propylene glycol, glycerol, trimethylolpropane, triethylene glycol, butanediols, pentanols, such as pentaerythritol, hexanols, polyethylene glycols, polypropylene glycols, polyethylene-propylene glycols, silicones, aromatic carboxylates (eg. dialkyl phthalates or trimellitates, benzoates or terephthalates) or aliphatic dicarboxylates (eg. dialkyl adipates, sebacates, azelaates, citrates and tartrates), fatty acid esters, such as glycerol mono-, di- or triacetate, or sodium diethylsulfosuccinate. The concentration of plasticizer is in general from 0.5 to 15, preferably from 0.5 to 5% by weight, based on the overall weight of the mixture.

The polymers suitable in accordance with the invention which are described above, and ancillary substances which are used where appropriate, are comprised in accordance with the invention by the term binder. A binder which is suitable in accordance with the invention thus comprises at least one binder of the type described above, with or without one or more of the abovementioned ancillary substances.

Conventional additives, whose total amount can be up to 100% by weight, based on the polymer, are, for example, extenders and bulking agents, such as silicates or diatomaceous earth, magnesium oxide, aluminum oxide, titanium oxide, stearic acid or its salts, for example the magnesium salt or the calcium salt, methylcellulose, sodium carboxymethylcellulose, talc, sucrose, lactose, cereal or corn starch, potato flour, polyvinyl alcohol, in particular in a concentration of from 0.02 to 50, preferably from 0.2 to 20% by weight, based on the overall weight of the mixture;
lubricants, such as aluminum stearate and calcium stearate, talc and silicones, in a concentration of from 0.1 to 5, preferably from 0.1 to 3% by weight, based on the overall weight of the mixture;
flow regulators, such as animal or vegetable fats, especially those in hydrogenated form and those which are solid at room temperature. These fats preferably have a melting point of 50° C. or more. Preference is given to triglycerides of the-$C_{12}$, $C_{14}$, $C_{16}$ and $C_{18}$ fatty acids. It is also possible to use waxes such as carnauba wax. These fats and waxes can advantageously be admixed alone or together with mono- and/or diglycerides or phosphatides, in particular lecithin. The mono- or diglycerides are preferably derived from the abovementioned fatty acid types. The overall amount of fat, waxes, monoglycerides, diglycerides and/or lecithins is from 0.1 to 30, preferably from 0.1 to 5% by weight, based on the overall weight of the composition for the particular layer;
colorants, such as azo dyes, organic or inorganic pigments or dyes of natural origin, preference being given to inorganic pigments in a concentration of from 0.001 to 10, preferably from 0.5 to 3% by weight, based on the overall weight of the mixture;
stabilizers, such as antioxidants, light stabilizers, hydroperoxide destroyers, free-radical scavengers and stabilizers against microbial attack.

It is also possible for wetting agents, preservatives, disintegrants, adsorbents, mold release agents and propellants as well as surfactants to be added (cf. eg. H. Sucker et al. Pharmazeutische Technologie, Thieme-Verlag, Stuttgart 1978).

For the purposes of the invention ancillary substances also mean substances for preparing a solid solution containing the pharmaceutical active ingredient. Examples of these ancillary substances are pentaerythritol and pentaerythritol tetraacetate, polymers, for example polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61 (1986) 69–88.

Pharmaceutical ancillary substances are also regarded as comprising additions of bases and acids to control the solubility of an active ingredient (see, for example, K. Thoma et al., Pharm. Ind. 51 (1989) 98–101).

The sole prerequisite for the suitability of ancillary substances is sufficient temperature stability.

For the purposes of the invention, active ingredients are all substances having a physiological action and minimal side effects provided they do not decompose under the processing conditions. In particular they are pharmaceutical active ingredients (for humans and animals), active ingredients for plant treatment, and active ingredients for feed and foodstuffs. The amount of active ingredient per dose unit and the concentration can each be varied within wide limits depending on efficacy and rate of release. The sole condition is that they are sufficient to attain the desired effect. Thus the concentration of active ingredient can be in particular in the range from 0.1 to 95, preferably from 20 to 80 and, especially, from 30 to 70% by weight (based on the overall weight of the dose form). Combinations of active ingredients can also be employed. For the purposes of the invention active ingredients can also be vitamins and mineral substances, as may be present in feed and foodstuffs, and also plant treatment agents and insecticides. The vitamins include vitamins of the A group, the B group, meaning not only $B_1$, $B_2$, $B_6$ and $B_{12}$ and nicotinic acid and nicotinamide but also compounds having vitamin B properties, for example adenine, choline, pantothenic acid, biotin, adenylic acid, folic acid, orotic acid, pangamic acid, carnitine, p-aminobenzoic acid, myo-inositol and lipoic acid, and also vitamin C, vitamins of the D group, E group, F group, H group, I and J group, K group and P group. Active ingredients for the purposes of the invention also include therapeutic peptides.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, phenoxifylline, phenoxymethylpenicillin, phenylephrine, phenylpropanolamine, phenytoin, piroxicam, polymyxin B, povidone iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatotropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine, zotepine.

Preferred active ingredients are ibuprofen (as racemate, enantiomer or enriched enantiomer), ketoprofen, flurbiprofen, acetylsalicylic acid, verapamil, paracetamol, nifedipine or captopril.

Specifically, solid solutions or dispersions may be formed. The terms solid solutions and solid dispersions are familiar to the skilled worker—from the literature cited at the outset, for example. In solid solutions of pharmaceutical active ingredients in polymers the active ingredient is in the form of a molecular dispersion in the polymer.

The solvent for the liquid form of the components is primarily water or a water-miscible organic solvent, or a mixture thereof with water. However, it is also possible to use water-immiscible or -miscible organic solvents. Particularly suitable water-miscible solvents are $C_1$–$C_4$-alkanols, such as ethanol, isopropanol or n-propanol, polyols, such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in each individual case depends on the component to be taken up and on the properties thereof. For example, pharmaceutical active ingredients are frequently employed in the form of a salt, which is generally soluble in water. Water-soluble active ingredients can, therefore, be employed as an aqueous solution or, preferably, can be taken up in the aqueous solution or dispersion of the binder. The same applies to active ingredients which are soluble in one of the abovementioned solvents, if the liquid form of the components employed is based on an organic solvent.

In general, the components are present in the solvent in as high a concentration as possible. The amount depends on the solvent employed and on the component.

It is possible in accordance with the invention for all the components to be combined to form a premix or for individual components to be added, at least in portions, at a later time, for example during extrusion. It is advisable, for example, for sensitive active ingredients or reactive components to be admixed only at a relatively late time during the process, so that they are exposed for as short a time as possible to high shear forces and/or temperatures during mixing and/or extrusion.

The mixing equipment which can be used is that also employed for mixing in plastics technology. Examples of suitable equipment are described, for example, in "Mischen beim Herstellen und Verarbeiten von Kunststoffen", H. Pahl, VdI-Verlag 1986. Particularly suitable mixing equipment comprises extruders and dynamic and static mixers, and also mixing tanks, single-shaft stirrers with stripper devices, especially paste stirrers, multishaft stirrers, especially PDSM mixers, solids mixers and, preferably, mixer/kneader reactors (eg. ORP, CRP, AP, DTP from List and Reaktotherm from Krauss-Maffei), trough mixers and internal mixers, or rotor/stator systems (eg. Dispax from Ika).

The mixing implement can be charged continuously or batchwise in a conventional way. Components in powder form can be introduced in a free feed, for example through a differential weigh feeder. Plastic compositions can be fed in directly front an extruder or through a gear pump, which is particularly advantageous at high viscosities and high pressures. Liquid media can be metered in by a suitable pump unit.

The steps of mixing and extrusion in the process can be carried out in the same equipment or in two or more items of equipment operating separately. A premix can be prepared in conventional mixing equipment as described above. Such a premix can then be fed directly into the extruder and subsequently extruded with or without the addition of other components.

The process according to the invention permits the use, as extruder, of single-screw machines, intermeshing screw machines or else multiscrew extruders, especially twin-screw extruders, which may be corotating or counterrotating, with or without kneading disks. Since extrusion entails the evaporation of a solvent, the extruders are generally equipped with an evaporation section. Particular preference is given to extruders of the ZKS series from Werner u. Pfleiderer.

Since, according to the invention, at least some of the components are employed in liquid form, the composition extruded contains a liquid, preferably water. If, for example, a premix which comprises at least one of the components in liquid form is prepared this liquid-containing composition can, for example, be fed into an extruder and subsequently extruded. It is, of course, also possible for at least part of the active ingredient, possibly as a dispersion or solution, not to be metered in until during extrusion, ie. in the extruder.

Another alternative comprises employing one component, for example the binder, alone or as a mixture with at least a portion of the active ingredient and/or at least some of the additives, in the form of a melt, it being possible to obtain such a melt by, for example, melting a solvent-free binder. The amounts of active ingredient and/or additive which may be present in the mixture can be added before, during or after the melting operation. Melting preferably takes place within the extruder used for extrusion.

In accordance with the invention it is also possible to produce multilayer pharmaceutical forms by coextrusion, in which case a plurality of mixtures of the above-described components are combined in one die in the extrusion to give the required layer structure of the multilayer pharmaceutical form. It is preferable to use different binders for different layers.

Multilayer drug forms preferably comprise two or three layers. They may be in open or closed form, in particular as open or closed multilayer tablets.

At least one of the layers contains at least one pharmaceutical active ingredient. It is also possible to include another active ingredient in a different layer. This has the advantage that two active ingredients which are incompatible with one another can be processed, or that the release characteristics of the active ingredient can be controlled.

Forming takes place by coextrusion, the mixtures from the individual extruders or other units being fed into a common coextrusion die and extruded. The shape of the coextrusion dies depends on the desired pharmaceutical form. For example, dies with a planar exit aperture, called slot dies, and dies with an annular cross section to their exit aperture are suitable. The design of die depends on the polymeric binder employed and on the desired pharmaceutical form.

Discharge from the extruder is generally followed by a final shaping operation. In this case it is possible to produce a large number of shapes depending on the extrusion die and the mode of shaping. For example, the extrudate can be shaped between a belt and a roll, between two belts or between two rolls, as described in EP-A-358 105, or by calendering in a calender having two molding rolls; see, for example, EP-A-240 904. Further forms can be obtained by extrusion and hot- or cold-cut pelletization of the extrudate, examples of such forms being small and uniformly shaped granules. Hot-cut pelletization results in general in lenticular tablets having a diameter of from 1 to 10 mm, while cold-cut pelletization normally results in cylindrical products having a length to diameter ratio of from 1 to 10 and a diameter of from 0.5 to 10 mm. In this way it is possible to produce monolayer drug forms, or else, by coextrusion, open or closed multilayer drug forms, examples being oblong tablets, coated tablets, pastilles and pellets. The resulting granules can also be ground subsequently to form powders and compressed into tablets in a conventional way. These drug forms can be rounded by conventional methods and/or provided with a coating in a subsequent process step.

The process of the invention has the advantage that the formation of dust can be suppressed through the use of solid components and thus that contamination of the production plant, and cleaning costs, can be reduced. This is particularly significant in the case of critical active ingredients having a high allergenic or toxic potential.

Another advantage of the process is that the problems caused to solids metering by agglomeration and sticking of the components are reduced. Furthermore, the risk of separation of solid components is eliminated. Yet another advantage is that the components, which are often supplied commercially in liquid form, can be incorporated directly without an additional preparation step.

In addition, unwanted reactions of the components in the course of storage in the form of a powder mixture can be avoided.

Finally, in the process of the invention the melt has a relatively low viscosity owing to its solvent content. Moreover, the solvent must be evaporated in the extruder, thereby cooling the melt because of the heat of evaporation required. The process is therefore very mild.

The examples which follow illustrate the invention without restricting it.

EXAMPLE 1

A twin screw extruder contained a melt of a mixture of polyvinylpyrrolidone with a K value of 30 and containing 20% by weight of ibuprofen. About 10 ml/min of a 30% by weight dispersion of a methacrylic acid/ethyl acrylate (1/1) copolymer were then metered continuously through a metering device in the cold region of the feed section into this extruder. This mixture was extruded under the following conditions:

Section 1: 60° C.

Section 2: 80° C.

Section 3: 100° C.

Section 4: 110° C.

Section 5: 100° C.

Section 6: 90° C.

Die: 110° C.

In addition, on section 5 there was a vacuum adapter allowing the solvent to be stripped off.

The result was a homogeneous composition which, after cooling, was ground and compressed into tablets.

EXAMPLE 2

A copolymer of 70% by weight vinyl acetate and 30% by weight N-vinylpyrrolidone of K value 40 (measured as a 1% strength solution in ethanol; for determining the K value see: H. Fikentscher, "Systematik der Cellulosen aufgrund ihrer Viskosität in Lösung", Cellulose-Chemie 13 (1932) 58–64 and 71–74) was prepared by free-radical polymerization in ethanolic solution (50% strength by weight). The active ingredient ibuprofen was added to the resulting ethanolic polymer solution to give a solution comprising 42.5% by weight of a polymer and 15.0% by weight ibuprofen in 42.5% by weight ethanol. This solution was extruded (throughput: 10 kg/h) directly in a ZSK 40 twin screw extruder at a processing temperature of 110° C. under devolatilizing conditions (40 mbar reduced pressure). The extrudate emerging from the die was cooled in a water bath and pelletized. The pellets obtained were transparent.

We claim:

1. A process for producing solid dose forms by mixing 50 to 99.9% by weight of at least one polymeric binder which is selected from poly (meth) acrylates, copolymers thereof with (meth) acrylic acid, polyvinyllactams, polyvinyl esters and copolymers of N-vinyllactams and vinyl esters, 0.1 to 50% by weight, of at least one active ingredient and optionally conventional additives, extruding the mixture to obtain a melt, whereby at least part of the polymeric binder is employed in the form of an aqueous dispersion and the dispersant is evaporated in the extruder, and shaping.

2. A process as claimed in claim 1, wherein the binder is selected from poly (meth)acrylates and copolymers thereof with (meth)acrylic acid.

3. A process as claimed in claim 1, wherein the binder is selected from polyvinyllactams and copolymers thereof with vinyl esters.

4. A process as claimed in claim 1, wherein a methacrylic acid/ethyl acrylate dispersion is employed as binder dispersion.

5. A process as claimed in claim 3, wherein a N-vinylpyrrolidone/vinyl acetate copolymer is employed as binder.

6. A process as claimed in claim 1, wherein the active ingredient is employed in the form of an aqueous solution or in the form of a solution in an organic solvent.

7. A process as claimed in claim 6, wherein a water-miscible solvent is used as an organic solvent.

8. A process as claimed in claim 7, wherein a solution of ibuprofen, ketoprofen, flurbiprofen, actylsalicyclic acid, verapmil, paracetamol, nifedipine or captopril as the active ingredient in a $C_1$–$C_4$-alkanol is employed.

9. A process as claimed in claim 1, wherein a dispersion of the polymeric binder is employed which contains the active ingredient in solution or in dispersion.

10. A process as claimed in claim 1, wherein at least part of the active ingredient is admixed during the extrusion process.

11. A process as claimed in claim 1, wherein part of the binder, alone or as a mixture with at least part of the active ingredient and/or at least part of the additives, is employed in the form of a polymer melt.

12. A process as claimed in claim 1, wherein the binder, alone or as a mixture with at least part of the active ingredient and/or at least part of the additives, is employed in the form of at least two dispersions or at least one dispersion and one solution.

13. A process as claimed in claim 1, wherein the mixture is coextruded to form a multilayer pharmaceutical form.

14. A process as claimed in claim 1, wherein all of the components of said solid dose form are combined before extrusion.

15. A process as claimed in claim 3, wherein said polyvinyllactams are selected from the group consisting of polyvinylpyrrolidone and copolymers of vinylpyrrolidone with vinyl esters.

16. A process as claimed in claim 7, wherein said water-miscible solvent is a $C_1$–$C_4$-alkanol.

* * * * *

UNITED STATES PATENT AND TRADEMARK OFFICE
CERTIFICATE OF CORRECTION

PATENT NO. : 6,221,368 B1
DATED : April 24, 2001
INVENTOR(S) : Breitenbach et al.

It is certified that error appears in the above-identified patent and that said Letters Patent is hereby corrected as shown below:

<u>Title page,</u>
Item [74], should be -- Keil & Weinkauf --

Signed and Sealed this

Eleventh Day of December, 2001

*Attest:*

*Nicholas P. Godici*

*Attesting Officer*

NICHOLAS P. GODICI
*Acting Director of the United States Patent and Trademark Office*